US012507678B2

(12) United States Patent
Paik et al.

(10) Patent No.: US 12,507,678 B2
(45) Date of Patent: Dec. 30, 2025

(54) ANIMAL MODEL FOR OXIDATIVE STRESS RESEARCH AND USE THEREOF

(71) Applicant: Industry-Academic Cooperation Foundation, Yonsei University, Seoul (KR)

(72) Inventors: Young-Ki Paik, Seoul (KR); Hae Lim Jeong, Seoul (KR); Jun Young Park, Seoul (KR); Soo Han Bae, Seoul (KR); Jeong Su Park, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 438 days.

(21) Appl. No.: 17/823,000

(22) Filed: Aug. 29, 2022

(65) Prior Publication Data

US 2023/0189770 A1 Jun. 22, 2023

(30) Foreign Application Priority Data

Aug. 27, 2021 (KR) ........................ 10-2021-0113959

(51) Int. Cl.
*A01K 67/0275* (2024.01)
*C12N 9/08* (2006.01)
*G01N 33/50* (2006.01)

(52) U.S. Cl.
CPC ........ *A01K 67/0275* (2013.01); *C12N 9/0065* (2013.01); *C12Y 111/01006* (2013.01); *G01N 33/5085* (2013.01); *A01K 2217/05* (2013.01); *A01K 2227/703* (2013.01); *A01K 2267/035* (2013.01); *G01N 2333/4353* (2013.01)

(58) Field of Classification Search
CPC .................................................. A01K 67/0275
See application file for complete search history.

(56) References Cited

FOREIGN PATENT DOCUMENTS

| | | | | |
|---|---|---|---|---|
| KR | 20160127588 A * | 4/2015 | ......... | A01K 67/0275 |
| KR | 10-2579513 B1 | 9/2023 | | |

OTHER PUBLICATIONS

C. elegans Sequencing Consortium *. "Genome sequence of the nematode C. elegans: a platform for investigating biology." Science 282.5396 (1998): 2012-2018 (Year: 1998).*

Jeong, Haelim, et al. "Deficiency in RCAT-1 function causes dopamine metabolism related behavioral disorders in Caenorhabditis elegans." International journal of molecular sciences 23.4 (Pub: Feb. 21, 2022): 2393 (Year: 2022).*

Wormbase Website, https://wormbase.org/species/c_elegans/strain/WBStrain00032185#03--10, Accessed Sep. 17, 2024 (Year: 2024).*

(Continued)

*Primary Examiner* — Tracy Vivlemore
*Assistant Examiner* — Brendan Thomas Tinsley
(74) *Attorney, Agent, or Firm* — Sterne, Kessler, Goldstein & Fox P.L.L.C.

(57) ABSTRACT

The present invention relates to an animal model for oxidative stress research and use thereof, and more specifically, the present invention can utilize a mutant of RCAT having a regulatory function for an antioxidant stress regulator in *Caenorhabditis elegans* and a human cell line expressing RCAT as animal and human cell line models for oxidative stress research, using the mutant and the human cell line.

6 Claims, 5 Drawing Sheets

Specification includes a Sequence Listing.

(56) References Cited

OTHER PUBLICATIONS

Shaulsky, Gad, Naomi Goldfinger, and Varda Rotter. "Alterations in tumor development in vivo mediated by expression of wild type or mutant p53 proteins." Cancer research 51.19 (1991): 5232-5237 (Year: 1991).*

Chakraborty, Sudipta, et al. "Oxidative stress mechanisms underlying Parkinson's disease-associated neurodegeneration in C. elegans." International journal of molecular sciences 14.11 (2013): 23103-23128 (Year: 2013).*

Ma, Liang, et al. "Caenorhabditis elegans as a model system for target identification and drug screening against neurodegenerative diseases." European Journal of Pharmacology 819 (2018) (Year: 2018).*

C. elegans Sequencing Consortium *. Science 282.5396 (1998): 2012-2018. (Year: 1998).*

Jeong, Haelim, et al. "Deficiency in RCAT-1 function causes dopamine metabolism related behavioral disorders in Caenorhabditis elegans." International Journal of Molecular Sciences 23 (2022): 2393 (Year: 2022).*

Chakraborty (Chakraborty, Sudipta, et al. International journal of molecular sciences 14.11 (2013): 23103-23128 (Year: 2013).*

Ma, Liang, et al. European Journal of Pharmacology 819 (2018): 169-180 (Year: 2018).*

Simmons, Steven O., et al. Current chemical genomics 5 (2011): 1. (Year: 2011).*

Brenner, S., "The Genetics of Caenorhabditis Elegans," Genetics 77(1):71-94, Oxford University Press, United Kingdom (May 1974).

Cao, S., et al., "Torsin-mediated protection from cellular stress in the dopaminergic neurons of Caenorhabditis elegans," J Neurosci 25(15):3801-3812, Society for Neuroscience, United States (Apr. 2005).

Drolet, J., "Investigating the omega-3 fatty acid DHA in acting as an exogenous regulator of the antioxidant response pathway in Parkinson's disease," University of Guelph, Ontario, Canada, 92 pages, (Nov. 2018).

Kampkotter, A., et al., "Effects of the Flavonoids Kaempferol and Fisetin on Thermotolerance, Oxidative Stress and FoxO Transcription Factor DAF-16 in the Model Organism Caenorhabditis Elegans," Archives of Toxicology 81(12):849-58, Springer-Verlag, Germany (Dec. 2007).

Lee, D.H., et al., "The hypertension drug, verapamil, activates Nrf2 by promoting p62-dependent autophagic Keapl degradation and prevents acetaminophen-induced cytotoxicity," BMB Rep 50(2):91-96, The Korean Federation of Science and Technology Societies, Seoul, South Korea (Feb. 2017).

Omura, D.T., et al., "Dopamine signaling is essential for precise rates of locomotion by C. elegans," PLoS One 7(6):e38649, PLoS, United States (Jun. 2012).

* cited by examiner

H-RACT: HA-tagged RCAT

F-Keap1: FLAG-tagged Keap1

M-Nrf2: MYC-tagged Nrf2

SEQUENCE LISTING

```
Sequence total quantity: 4
SEQ ID NO: 1           moltype = DNA  length = 2290
FEATURE                Location/Qualifiers
source                 1..2290
                       mol_type = genomic DNA
                       organism = Caenorhabditis elegans
SEQUENCE: 1
gccaattgtg atttttccag catcgtttgg tggcatcgta tccacatcaa ctacgttgat  60
atattcatct tcttccgcag tttctgaatc cacaacttgt tcgcgatgtt ttgcagaatt  120
attttctgaa gtagttgcct gaaaattcaa tttttgagtt ttcagaacaa tttaaccgtc  180
tgtaaacctt ttcaatgtta tcaggtttgc tttgcatcct tggaattttc gccttaacct  240
catcatcatc ttcttctctc ggttctttcg tactatctgc agcaacggct cgccgctctt  300
tcaaactaat cggaatcgca gaagattttg cagtgtccgt taaaaaacca agcttctccc  360
gttctctatt gtaccgaact gtgatatttc tgcaaaaaac attatatttg cctactgttt  420
cggatgatta ccctcaccta atatcattct ttgagatata ttttaattta cactcgtagt  480
ccttgtactc attccgaata aagaagaaga tctgatcaga agtccatccc aagtcaatta  540
gctcacgaac atatttttcc tgagattcgg tgagccatag aagtttgtga tcaagatcat  600
gtccgatatg agtaaagcat ccagttgccc aagttgaacc gtcctcttct gttgtgacct  660
gaaatatttt tcaaaatttt aaaacaaatt ttttaaaaaa tgttttactt tcaaatatgc  720
tgtacaagtc tggtcaatct tcctgggatt cgatttcctg gattttgcga cactttgata  780
ctttccgaca cgatgacacc tataaagtgt ttctccagca tgtcctgtac gttttgtcaa  840
cgatgtacat gtgtcctcct gtctctgatc gaaccattcc taaaattaga tttttgtcat  900
tttatcgaga atatttaaaa accttaaact ggtctcttga ttggaaaaac tctcgttcta  960
aattaaactt ctgatcatgg gacatgtgtt cttgacggca atgcagtaaa aattcatcca  1020
acgactctga tgtactcgaa cattcgggac attttaaatt acatccacga tattttcctg  1080
gtagttgcat taacgagaat tttgaaggtt tttcaataat ggtggcaatt tggctgaaaa  1140
tcatagtttt tgacagaaac ctttattttt tctaattcca accattcctg cgttaaatga  1200
tgtggctgga ttggacgaga agcttgtcga tgtggcggaa tattcatctc gaaactatct  1260
ccagatgatg tggatggttt ttgtgtagat tctttagttt cattgatatc atattcattg  1320
attccaacaa cttcttcttc tccttcaaca atcatttcat ctatataaac atcaagatgc  1380
tcgttgtcat gttgcggttg ttcagtgcac atctgcaaga tccaattttt atatttagtt  1440
ttccagaaga atagggttgt attacctttt tatgctgaac cagatgcttg acacttcgaa  1500
atatcatcct acagtggcag caaacaaacg atgtgctaga tgctcggctc tttttttcag  1560
attttatagc ggcaatcagt tcctgacaat cttcagttgt ccaattatga atctgtgtca  1620
tgtgacgata gatattcttt tgtagacatg ttagggcgca ttctgggcat cgtatctgat  1680
caataatgca ggactcgagt tcgataggat ttgtggtcat ttcctgcaat tttcaaacat  1740
ttctatatcc ggaagtgaaa aatacgtgtt ttcaaggatt atcagttcca gaaaaattgg  1800
cattcacttt tgtgaatttt tttgcgttaa attctaaaag tttatggaaa attgacaaaa  1860
atcagaggaa aatagaaaat taaaacgatt ggtaggattt acgctcgtaa atcctgtcac  1920
ttcgacgcgt cgcgtgttcg cgttgcgtgt ctgcaagtcc gctccattgc agagaacttt  1980
aagcgcgatg tttgaaataa tattttttgt gtcttataaa gctttattaa atacaactga  2040
agttgcaatt ttttttcaga ttggaccgag agagaaaact ttttatgaat attttcaagc  2100
ggttaaaaaa tcaatttaaa agggaagaaa gtggcgaaac ttcttcagtg tgtagacttc  2160
ctcatggcgg agagaattga cagattaaaa cttccaaaaa aatctaattt ctagaaacgt  2220
atacgtgaaa ctgtacttgc aattcgatat tctcgctata ttttttgcaa agatttattg  2280
```

-continued

```
ttctgaacgg                                                          2290

SEQ ID NO: 2             moltype = DNA  length = 3460
FEATURE                  Location/Qualifiers
source                   1..3460
                         mol_type = genomic DNA
                         organism = Caenorhabditis elegans
SEQUENCE: 2
ttgaaatatc ataaatcttg tcaggcagct gtgccgaaaa aattgttttt taatctacga  60
aaatatcgaa attgtttccc gtaaatcgac aaggggctga ggtttctaga ccacacggcc  120
gtgtactcct ctcggacaat ggattaattt tatctgctat aattttattt ttcgattttc  180
acacgttttc cagtcaaatt tcgtaatatt tcataatttt ttatcattta agactcgaaa  240
atgtcgataa acttcacgag gacaccaaga ttattacttg acacagtagg taattccatt  300
tttctagttt ttttcgaatt taaataatta aagttaattt cagcccatta ctcatcattc  360
ttggaaagca caaagcttgt aaagactcgg gaagtgaaga aaccacccag atatccaaac  420
ttttcactga aaaaagatac gaaaagtggg gagattgctt actttttggc aaaataactt  480
tattttaatc ttttcagatc aaaaaatgag ccagcacttt gattatcttc tagtattaga  540
cttcgaagcc acgtgtcaag ataactggaa agggccgatg catccagtcc aagaaatcat  600
cgaattccca gtggtccagc tctcgacggc tgattggagt gaaattcgtc gttttcatca  660
atacgttaag ccgacggaat gtccaaggct cacatctttc tgcacatctt taacaggaat  720
tattcaggtt tttaatgcaa aaatttcgag gaaaaaatgc taaaattcca ggaaatggtt  780
gacgaaaaac cgacgcttcc acaagtttta tcggaatttg atagctggct gaaagaggat  840
tctcgactgg aaaagggcaa atttgcattc gtcacttgtg gagattggga tctgaaagtc  900
gcgctgccga atgaggcgaa atttaagaat attggaattc cagagtaaat tttttagagt  960
aaaactgaca atttgaggct gaaaattcgt acaatttgac tctaaaaatc tgaaatttca  1020
ttaaaaaaca atcattttg tcccacgaac cgcacaaatc caaacaaatt gtccttcagg  1080
tacttcaatc aatggatcaa cgtgaaaaag gcttctgcgg agcacacaaa tcatttcgcg  1140
aaaggaatag cccagcttct ggccatctac aagctgcaac atcaggtttt ctactgaaat  1200
tctgaaatct cagcaaaatt ctaattttcc agggtcgcca ccacagtgga attgatgacg  1260
tggcaaatat ctgcgaaatt gtccggtgtt tgggcatgaa cgggcacaac tatcaaatca  1320
caggctccaa agacacaatg acgcggaggg tgttcagaga tgcgaggaaa taatttttgt  1380
cgatttttca gcaatatgta ttaatacgaa atattgactt ttccgccatt tttccgttca  1440
gaacaataaa tctttgcaaa aaatatagcg agaatatcga attgcaagta cagtttcacg  1500
tatacgtttc tagaaattag attttttttgg aagttttaat ctgtcaattc tctccgccat  1560
gaggaagtct acacactgaa gaagtttcgc cactttcttc ccttttaaat tgattttta  1620
accgcttgaa aatattcata aaaagtttc tctctcggtc caatctgaaa aaaaattgca  1680
acttcagttg tatttaataa agctttataa gacacaaaaa atattatttc aaacatcgcg  1740
cttaaagttc tctgcaatgg agcggacttg cagacacgca acgcgaacac gcgacgcgtc  1800
gaagtgacag gatttacgag cgtaaatcct accaatcgtt ttaattttct attttcctct  1860
gatttttgtc aattttccat aaacttttag aatttaacgc aaaaaaattc acaaaagtga  1920
atgccaattt ttctggaact gataatcctt gaaaacacgt atttttcact tccggatata  1980
gaaatgtttg aaaattgcag gaaatgacca caaatcctat cgaactcgag tcctgcatta  2040
ttgatcagat acgatgccca gaatgcgccc taacatgtct acaaaagaat atctatcgtc  2100
acatgacaca gattcataat tggacaactg aagattgtca ggaactgatt gccgctataa  2160
aatctgaaaa aaagagccga gcatctagca catcgtttgt ttgctgccac tgtaggatga  2220
tatttcgaag tgtcaagcat ctggttcagc ataaaaaggt aatacaaccc tattcttctg  2280
gaaaactaaa tataaaaatt ggatcttgca gatgtgcact gaacaaccgc aacatgacaa  2340
cgagcatctt gatgtttata tagatgaaat gattgttgaa ggagaagaag aagttgttgg  2400
aatcaatgaa tatgatatca atgaaactaa agaatctaca caaaaaccat ccacatcatc  2460
gccaattgtg atttttccag catcgtttgg tggcatcgta tccacatcaa ctacgttgat  2520
atattcatct tcttccgcag tttctgaatc cacaacttgt tcgcgatgtt ttgcagaatt  2580
attttctgaa gtagttgcct gaaaattcaa tttttgagtt ttcagaacaa tttaaccgtc  2640
tgtaaacctt ttcaatgtta tcaggtttgc tttgcatcct tggaattttc gccttaacct  2700
catcatcatc ttcttctctc ggttctttcg tactatctgc agcaacggct cgccgctctt  2760
tcaaactaat cggaatcgca gaagattttg cagtgtccgt taaaaaacca agcttctccc  2820
gttctctatt gtaccgaact gtgatatttc tgcaaaaaac attatatttg cctactgttt  2880
cggatgatta ccctcaccta atatcattct ttgagatata ttttaattta cactcgtagt  2940
ccttgtactc attccgaata gaaaaattgg cattcacttt tgtgaatttt tttgcgttaa  3000
attctaaaag tttatggaaa attgacaaaa atcagaggaa aatagaaaat taaaacgatt  3060
ggtaggattt acgctcgtaa atcctgtcac ttcgacgcgt cgcgtgttcg cgttgcgtgt  3120
ctgcaagtcc gctccattgc agagaacttt aagcgcgatg tttgaaataa tattttttgt  3180
gtcttataaa gctttattaa atacaactga agttgcaatt tttttcaga ttggaccgag  3240
agagaaaact ttttatgaat attttcaagc ggttaaaaaa tcaatttaaa agggaagaaa  3300
gtggcgaaac ttcttcagtg tgtagacttc ctcatggcgg agagaattga cagattaaaa  3360
cttccaaaaa aatctaattt ctagaaacgt atacgtgaaa ctgtacttgc aattcgatat  3420
tctcgctata tttttgcaa agatttattg ttctgaacgg                          3460

SEQ ID NO: 3             moltype = DNA  length = 1440
FEATURE                  Location/Qualifiers
source                   1..1440
                         mol_type = other DNA
                         note = RCAT cDNA
                         organism = synthetic construct
SEQUENCE: 3
atgaccacaa atcctatcga actcgagtcc tgcattattg atcagatacg atgcccagaa  60
tgcgccctaa catgtctaca aaagaatatc tatcgtcaca tgacacagat tcataattgg  120
acaactgaag attgtcagga actgattgcc gctataaaat ctgaaaaaaa gagccgagca  180
tctagcacat cgtttgtttg ctgccactgt aggatgatat ttcgaagtgt caagcatctg  240
gttcagcata aaaagatgtg cactgaacaa ccgcaacatg acaacgagca tcttgatgtt  300
```

-continued

```
tatatagatg aaatgattgt tgaaggagaa gaagaagttg ttggaatcaa tgaatatgat  360
atcaatgaaa ctaaagaatc tacacaaaaa ccatccacat catctggaga tagtttcgag  420
atgaatattc cgccacatcg acaagcttct cgtccaatcc agccacatca tttaacgcag  480
gaatgccaaa ttgccaccat tattgaaaaa ccttcaaaat tctcgttaat gcaactacca  540
ggaaaatatc gtggatgtaa tttaaaatgt cccgaatgtt cgagtacatc agagtcgttg  600
gatgaatttt tactgcattg ccgtcaagaa cacatgtccc atgatcagaa gtttaattta  660
gaacgagagt ttttccaatc aagagaccag tttaaggaat ggttcgatca gagacaggag  720
gacacatgta catcgttgac aaaacgtaca ggacatgctg gagaaacact ttataggtgt  780
catcgtgtcg gaaagtatca aagtgtcgca aaatccagga aatcgaatcc caggaagatt  840
gaccagactt gtacagcata tttgaaagtc acaacagaag aggacggttc aacttgggca  900
actggatgct ttactcatat cggacatgat cttgatcaca aacttctatg gctcaccgaa  960
tctcaggaaa aatatgttcg tgagctaatt gacttgggat ggacttctga tcagatcttc  1020
ttctttattc ggaatgagta caaggactac gagtgtaaat taaaatatat ctcaaagaat  1080
gatattagaa atatcacagt tcggtacaat agagaacggg agaagcttgg ttttttaacg  1140
gacactgcaa aatcttctgc gattccgatt agtttgaaag agcggcgagc cgttgctgca  1200
gatagtacga aagaaccgag agaagaagat gatgatgagg ttaaggcgaa aattccaagg  1260
atgcaaagca aacctgataa cattgaaaag gcaactactt cagaaaataa ttctgcaaaa  1320
catcgcgaac aagttgtgga ttcagaaact gcggaagaag atgaatatat caacgtagtt  1380
gatgtggata cgatgccacc aaacgatgct ggaaaaatca caattggctt aaatttttag  1440

SEQ ID NO: 4            moltype = DNA  length = 1290
FEATURE                 Location/Qualifiers
source                  1..1290
                        mol_type = other DNA
                        note = ok1745 deletion region
                        organism = synthetic construct
SEQUENCE: 4
aagaagaaga tctgatcaga agtccatccc aagtcaatta gctcacgaac atatttttcc  60
tgagattcgg tgagccatag aagtttgtga tcaagatcat gtccgatatg agtaaagcat  120
ccagttgccc aagttgaacc gtcctcttct gttgtgacct gaaatatttt tcaaaatttt  180
aaaacaaatt ttttaaaaaa tgttttactt tcaaatatgc tgtacaagtc tggtcaatct  240
tcctgggatt cgatttcctg gattttgcga cactttgata ctttccgaca cgatgacacc  300
tataaagtgt ttctccagca tgtcctgtac gttttgtcaa cgatgtacat gtgtcctcct  360
gtctctgatc gaaccattcc taaaattaga tttttgtcat tttatcgaga atatttaaaa  420
accttaaact ggtctcttga ttggaaaaac tctcgttcta aattaaactt ctgatcatgg  480
gacatgtgtt cttgacggca atgcagtaaa aattcatcca acgactctga tgtactcgaa  540
cattcgggac attttaaatt acatccacga tatttcctg gtagttgcat taacgagaat  600
tttgaaggtt tttcaataat ggtggcaatt tggctgaaaa tcatagtttt tgacagaaac  660
ctttattttt tctaattcca accattcctg cgttaaatga tgtggctgga ttggacgaga  720
agcttgtcga tgtggcggaa tattcatctc gaaactatct ccagatgatg tggatggttt  780
ttgtgtagat tctttagttt cattgatatc atattcattg attccaacaa cttcttcttc  840
tccttcaaca atcatttcat ctatataaac atcaagatgc tcgttgtcat gttgcggttg  900
ttcagtgcac atctgcaaga tccaattttt atatttagtt ttccagaaga atagggttgt  960
attacctttt tatgctgaac cagatgcttg acacttcgaa atatcatcct acagtggcag  1020
caaacaaacg atgtgctaga tgctcggctc ttttttcag attttatagc ggcaatcagt  1080
tcctgacaat cttcagttgt ccaattatga atctgtgtca tgtgacgata gatattcttt  1140
tgtagacatg ttagggcgca ttctgggcat cgtatctgat caataatgca ggactcgagt  1200
tcgataggat ttgtggtcat ttcctgcaat tttcaaacat ttctatatcc ggaagtgaaa  1260
aatacgtgtt ttcaaggatt atcagttcca                                 1290
```

ANIMAL MODEL FOR OXIDATIVE STRESS RESEARCH AND USE THEREOF

CROSS-REFERENCE TO RELATED APPLICATION

This application claims priority to and the benefit of Korean Patent Application No. 10-2021-0113959, filed on Aug. 27, 2021, the disclosure of which is incorporated herein by reference in its entirety.

REFERENCE TO SEQUENCE LISTING SUBMITTED ELECTRONICALLY

The content of the electronically submitted sequence listing (Name: 5142_0010001_SequenceListing_ST26.xml; Size: 11,174 bytes; and Date of Creation: Sep. 17, 2025) is herein incorporated by reference in its entirety.

BACKGROUND

Field of the Invention

The present invention relates to a use of a deletion mutant for an RCAT gene having a regulatory function for an oxidation stress in *Caenorhabditis elegans* and a human cell line transfected with the RCAT gene as an animal model for oxidative stress research.

Discussion of Related Art

*Caenorhabditis elegans* lives in soil, has a body size of about 1 mm, and is the first multicellular organism whose DNA sequence has been fully elucidated. *Caenorhabditis elegans* has about 19,000 genes similar to humans. *C. elegans* has many unique features that make it an ideal model organism, such as a convenient inbreeding reproductive mode (i.e., hermaphroditic), a short life span (2~3 weeks), a large brood size (>300 progeny), a variety of readily produced genetic mutants, and ease of cultivation in the laboratory Its body is transparent in which the number of somatic cells and nerve cells is as small as 1,000 and 320, respectively. Oxidative stress or reactive oxygen species (ROS) is produced during energy metabolism or by bacterial infection and heavy metals. Oxidative stress is known to contribute to the progression of various diseases such as metabolic diseases, neurodegenerative diseases, aging, cancer and diabetes. Nrf2/SKN-1, which is well known as a master transcription factor for controlling oxidative stress, carries out cellular defense functions during the detoxification process in animals including humans. Although many studies have been conducted on the regulation of oxidative stress where Nrf2/SKN plays an important role, the transcriptional regulation of Nrf2/SKN-1 is remained elusive in animals including *C. elegans*. That is, although extensive studies of searching a regulator for Nrf2/SKN1, there still remains largely unknown for the presence of biological regulator of Nrf2/SKN-1.

SUMMARY OF THE INVENTION

It is an object of the present invention to provide an animal model for oxidative stress research, including a deletion mutant of regulator of cat (RCAT, R02D3.7) and the mammalian cell lines overexpressing the nematode RCAT gene.

It is another object of the present invention to provide a model animal for use of RCAT.

It is still another object of the present invention to provide a method for screening an antioxidant drug using the animal model.

To achieve these objectives, the present invention provides an animal model for oxidative stress research, including a regulator of cat (RCAT) gene deletion mutant represented by a base sequence of SEQ ID NO: 1.

The present invention also provides an antioxidant composition including a regulator of cat (RCAT) gene represented by a base sequence of SEQ ID NO: 2 or 3, or a protein encoded therefrom.

The present invention also provides a method for screening an antioxidant drug, the method including:

handling of an animal model for oxidative stress research, including a regulator of cat (RCAT) gene deletion mutant represented by a base sequence of SEQ ID NO: 1 with an antioxidant candidate drug; and measuring whether the generation amount of reactive oxygen species (ROS) is reduced in the animal model.

According to the present invention, an RCAT mutant including the RCAT gene deletion mutant may be used not only as an animal model for oxidative stress research, but also in the screening of an antioxidant drug because the generation amount of reactive oxygen species (ROS) is increased.

According to the present invention, a human HEK293T cell line transfected with RCAT derived from *Caenorhabditis elegans* and Nrf2 may be used not only as an animal cell model for oxidative stress research, but also in the screening of an antioxidant drug because the transcriptional activity of an antioxidant factor Nrf2 is increased by the action of RCAT originating from *Caenorhabditis elegans*.

BRIEF DESCRIPTION OF THE DRAWINGS

The above and other objectives, features and advantages of the present invention will become more apparent to those of ordinary skill in the art by describing in detail exemplary embodiments thereof with reference to the accompanying drawings, in which:

FIG. 3 shows that the levels of SKN-1 and detoxification genes are directly regulated in the presence of RCAT;

DETAILED DESCRIPTION OF EXEMPLARY EMBODIMENTS

Hereinafter, the configuration of the present invention will be specifically described.

The present invention relates to an animal model for oxidative stress research, including a regulator of cat (RCAT) gene deletion mutant represented by SEQ ID NO: 1.

The regulator of cat (RCAT) is a common name for R02D3.7, which was shown to suppress transcriptional expression of cat-1 and cat-2 ('cat' means catecholamine), that are dopamine metabolism-related enzyme genes of *Caenorhabditis elegans*. However, the biological function, action mechanism and its association with human diseases thereof and the degree of utilization using this gen have not been well elucidated. The present inventors discovered the ability of RCAT to transcriptionally regulate cat-1 or cat-2, and based on this, they named R02D3.7 as regulator of cat (RCAT).

The RCAT gene deletion mutant has a deletion of five exons including the start codon and some promoter regions as shown in the nucleotide sequences of SEQ ID NO: 2, and the aforementioned deletion site may be represented by a base sequence of SEQ ID NO: 4. Preferably, the RCAT gene deletion mutant may be represented by a base sequence of SEQ ID NO: 1.

Figure 2:
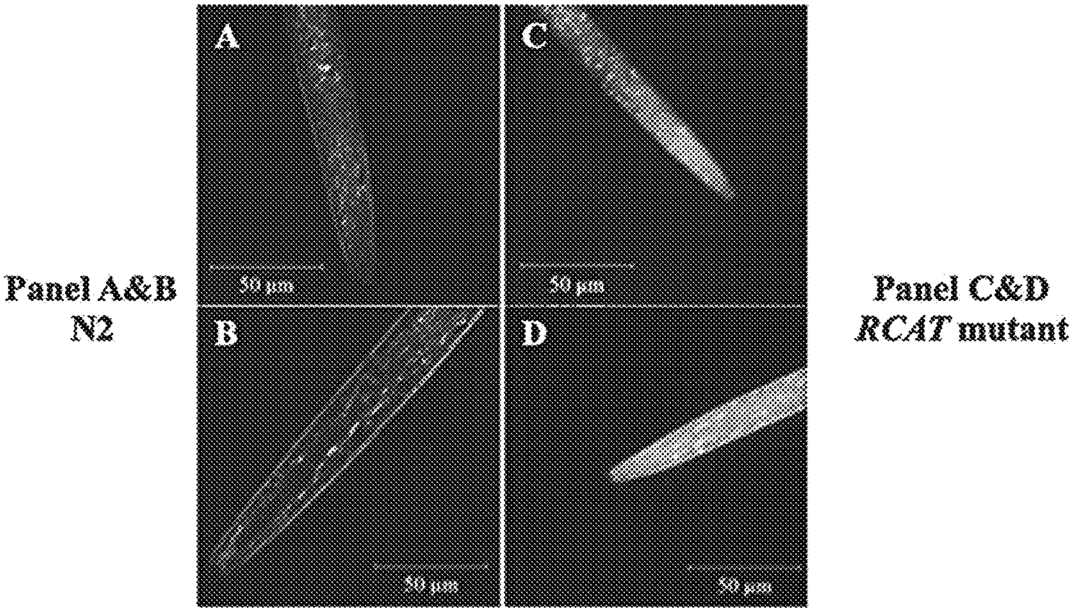
FIG. 2 illustrates the results from DCFDA analysis in that a reactive oxidative species (ROS) level is highly elevated in a *Caenorhabditis elegans* RCAT deletion mutant, meaning that the greener the fluorescence, the higher the ROS level.
Figure 3:
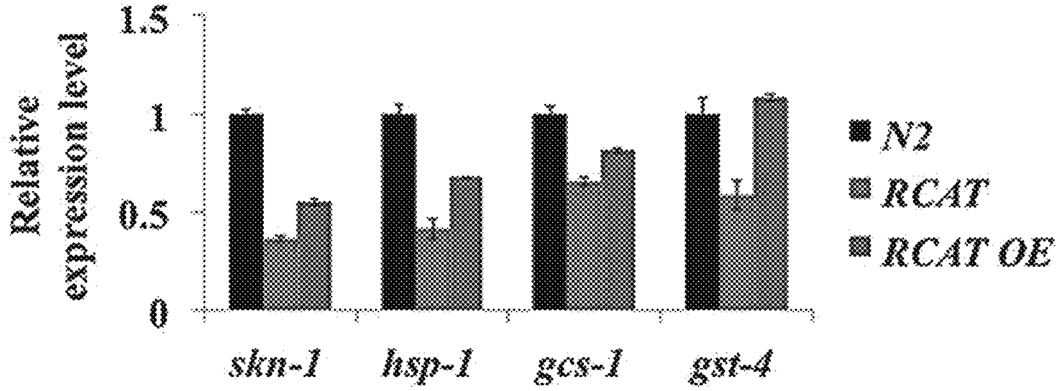
FIG. 3 is a graph obtained from qRT-PCR analysis in that the expression levels of detoxification genes activated by oxidative stress, such as SKN-1 and its downstream targets, GCS-1 and GST-4, are decreased in a *Caenorhabditis elegans* RCAT deletion mutant but increased again in a mutant strain where RCAT is overexpressed.

According to an exemplary embodiment of the present invention, the RCAT mutant generated more ROS in non-dopaminergic cells of *Caenorhabditis elegans* (FIG. 2). Further, it was found that the expression of oxidative stress-related genes known to be regulated by SKN-1 (homolog of human Nrf2) of *Caenorhabditis elegans*, which is an oxidative stress-related transcription factor associated with ROS generation, was reduced in an RCAT mutant compared to that in N2 wild type worms, and the reduction in expression was partially recovered in an RCAT overexpressed strain (FIG. 3).

It is known that human Nrf2 binds to Keap1, which is then degraded under the normal physiological conditions. However, when cells are under the oxidative stress condition, Nrf2 is released from the Nrf2-Keap1 complex and then enters the nucleus, thereby suppresses the transcription of oxidative stress-related genes.

Figure 5:
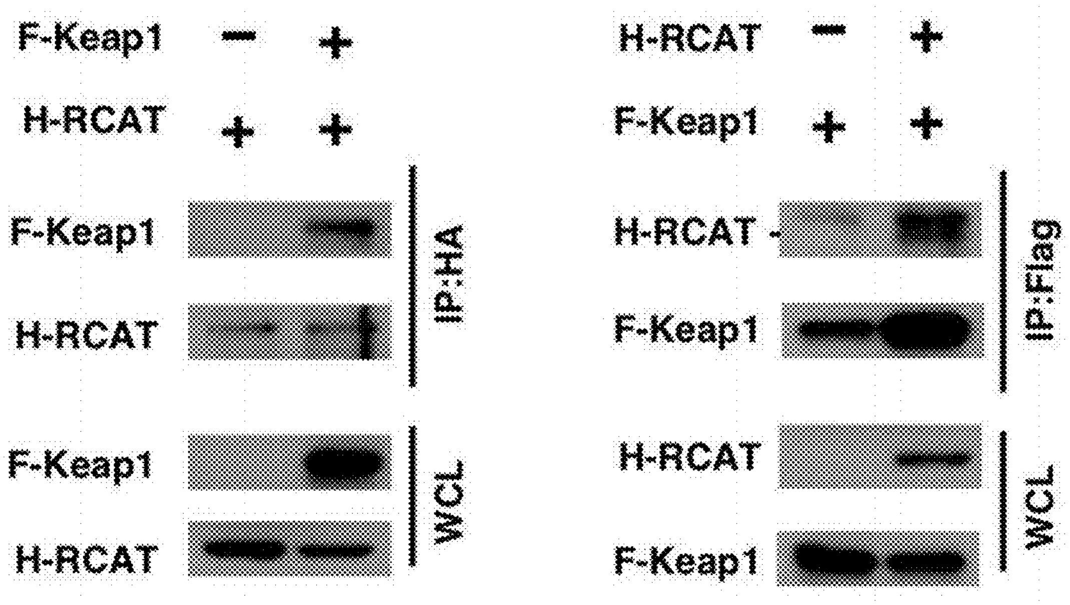
FIG. 5 shows the results of expressing FLAG-tagged Keap1 and HA-tagged RCAT in a human HEK293T cell line where the two proteins actually bind as assessed by immunoprecipitation (IP). The left side shows the result of IP using an HA-antibody, while the right side displays the result of IP using a FLAG antibody. Since both Keap1 and RCAT are detected in both experiments, it is confirmed that the two proteins are physically interacted.
Figure 6:
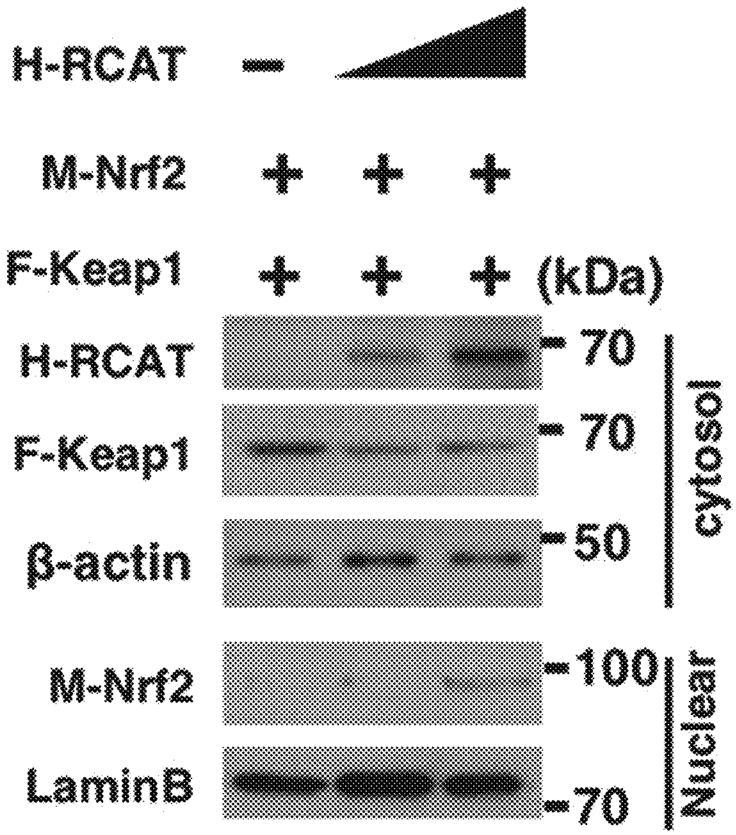
FIG. 6 shows the results of western blot analysis to show whether free Nrf2 is actually generated by the action of RCAT in a human HEK293T cell line and enters the nucleus.

Inventors investigated whether RCAT and Nrf2 can interact and work together in a human HEK293T cell line as seen in *C. elegans*, they found that when RCAT was added, Keap1 competitively interacted with RCAT instead of Nrf2, and accordingly, unbound Nrf2s then freely entered the nucleus (FIGS. 5 and 6).

Figure 7:
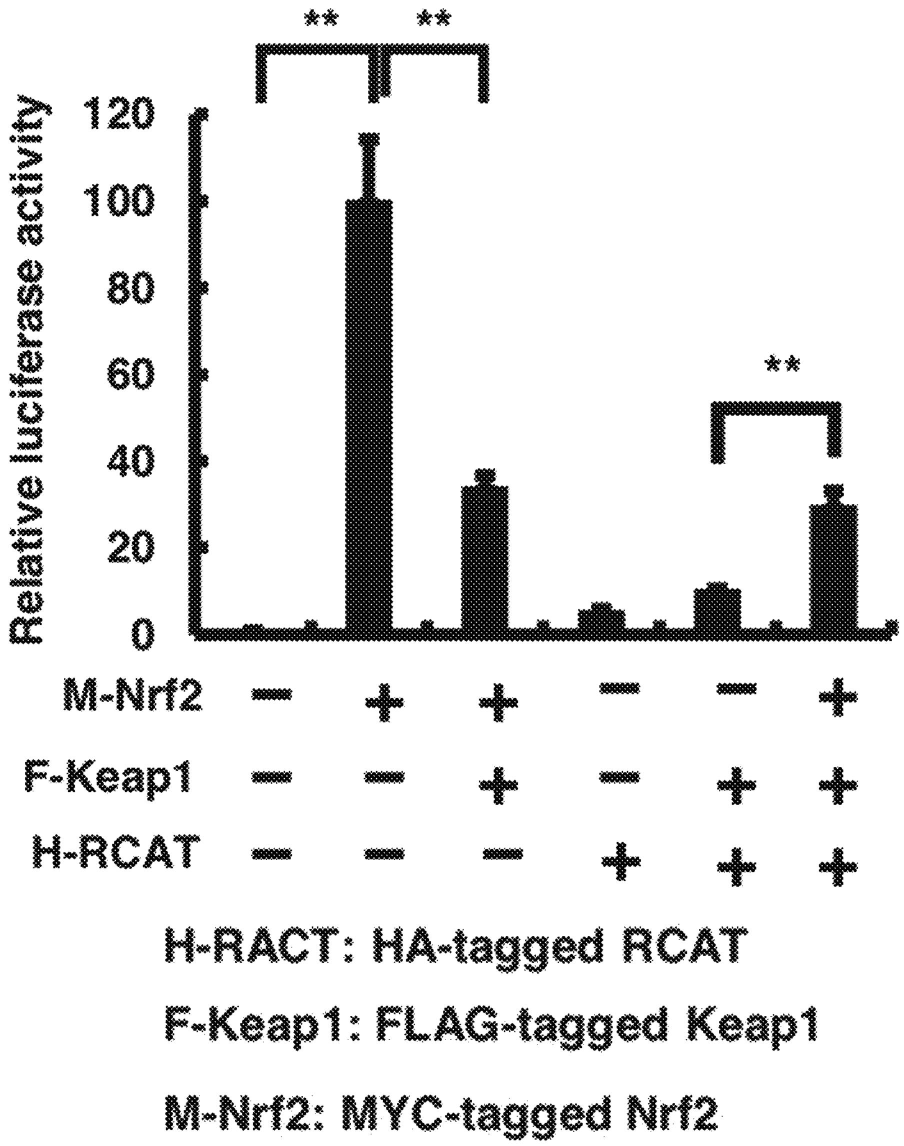
FIG. 7 shows the luciferase reporter analysis results for the transactivation activity of Nrf2 by RCAT overexpressed in human HEK293T cell line.

It was also observed that binding of RCAT to Keap1 causes degradation of Keap1 in the human HEK293T cell line, thereby enhances the transactivation of Nqo-1 by Nrf2 (FIG. 7).

Therefore, RCAT is a novel regulator that controls antioxidant Nrf2/SKN-1 in non-dopaminergic cells and an RCAT deletion mutant has an increased level of ROS compared to the wild type, and thus may be useful for numerous studies as an animal model in studying oxidative stress.

Therefore, the animal model may be a *Caenorhabditis elegans* mutant including an RCAT gene deletion mutant; or a human HEK293T cell line overexpressing RCAT and Nrf2.

The *Caenorhabditis elegans* mutant including the RCAT gene deletion mutant may have an increased level of reactive oxygen species (ROS) compared to the wild-type N2 *Caenorhabditis elegans*. Preferably, the animal model may be *Caenorhabditis elegans* R02D3.7 (ok1745).

Furthermore, the human HEK293T cell line overexpressing RCAT and Nrf2/SKN-1 may be a human HEK293T cell line transfected with an RCAT gene of *Caenorhabditis elegans* and an Nrf2/SKN-1 gene. The human HEK293T cell line may increase the transcriptional activity of an antioxidant transcription factor Nrf2/SKN-1 by the action of RCAT originating from *Caenorhabditis elegans*.

In an exemplary embodiment of the present invention, the RCAT gene may be overexpressed by inserting an RCAT cDNA represented by a base sequence of SEQ ID NO: 3 into an expression vector, and then transfecting the expression vector into a human HEK293T cell line. Specifically, a human HEK293T cell line is transfected with Flag-Keap1 (Addgene, MA, USA), pCDNA3-Myc3-Nrf2 (Addgene, MA, USA), or pcDNA3.1-HA-RCAT, wherein the expression vector pCDNA3.1-HA-RCAT which is constructed by conjugating *Caenorhabditis elegans* RCAT cDNA with pcDNA3.1-HA (Addgene, MA, USA).

As used herein, the term "animal model" refers to an animal that mimics or simulates the characteristics of human diseases, meaning that the animal model may be used for the disease research in which it is difficult to test and apply therapeutic method.

The present invention also relates to an antioxidant composition including a regulator of cat (RCAT) gene represented by a base sequence of SEQ ID NO: 2 or 3, or a protein encoded therefrom.

Nrf2/SKN-1, which is well known as a master transcription factor, carries out cell defense functions during the detoxification process of oxidative stress in animals including humans. It is known that Nrf2/SKN-1 binds to Keap1 and then this Nrf2/Keap1 complex to be degraded under a normal physiological condition. However, under the oxidative stress condition, RCAT binds Keap1, leaving free Nrf2, that can enter the nucleus, thereby suppressing the transcription of oxidative stress-related genes.

According to exemplary embodiments of the use of the present invention, as a result of expressing RCAT and Nrf2 in an HEK293T cell line, one can examine whether *C. elegans* RCAT and Nrf2/SKN-1 can interact and exert their anti-oxidation function. It was found that when RCAT was added, Keap1 bound to RCAT instead of Nrf2, and accordingly, more Nrf2s that freely enter the nucleus. In addition, it was observed that RCAT bound to Keap1 caused degradation of Keap1 in the human HEK293T cell line, thereby increasing the transcriptional activity of NQO-1, a mammalian NAD(P)H dehydrogenase, by Nrf2. Therefore, RCAT is a regulatory factor that suppresses the expression of antioxidant Nrf2/SKN-1 in non-dopaminergic cells, and thus may be used as an antioxidant component.

The present invention also relates to a method for screening an antioxidant drug, the method including: microinjection or addition of anti-oxidant drug candidates into the growth media (plate for *C. elegans*, culture media for human mammalian cells) where an animal model (i.e., *C. elegans* RCAT mutant strain or RCAT overexpressed HEK293 cell lines) can take up biological for response to drugs. Herein RCAT gene deletion mutant is represented by a base sequence of SEQ ID NO: 1 with an antioxidant candidate drug; and measuring whether a generation amount of ROS is reduced in the animal model.

The animal model of the present invention is an RCAT gene deletion mutant, and is characterized by an increased generation amount of ROS. Therefore, the antioxidant candidate drug may be brought into contact with the RCAT mutant to select the candidate drug in which the ROS generation amount of the RCAT mutant is reduced as an antioxidant drug. Preferably, the animal model may be *Caenorhabditis elegans* R02D3.7 (ok1745).

The antioxidant candidate drug may include any molecules such as proteins, peptides, small organic molecules, polysaccharides, polynucleotides and a wide range of compounds. Such candidate materials also include synthetic materials as well as natural products.

Hereinafter, the present invention will be described in more detail through the Examples according to the present invention, but the scope of the present invention is not limited by the Examples as suggested below.

<EXAMPLE 1> IDENTIFICATION OF CHARACTERISTICS OF *C. elegans* RCAT MUTANT

1. Strain

The species of *C. elegans* used in the present experiment is as follows: Wild type: Bristol (N2 species); RCAT [R02D3.7 (ok1745)]; RCAT OE [R02D3.7::GFP, rol-6]

Unless otherwise stated, *C. elegans* was cultured in a solid nematode growth medium (NGM) containing OP50 at 20° C. using a standard method, and a synchronized culture was prepared by treating an adult (gravid adult) with hypochlorite as previously described (Brenner, S. *Genetics* 77, 71-94, 1974).

2. ROS Analysis

ROS generation levels in wild type and mutants of *C. elegans* were measured using 2,7-dicholorodihydro-fluorescein-diaceate (DCFDA). The ROS measurement method was performed according to a previously established protocol (Kampkφtter, A. et al. *Arch Toxicol* 81, 849-858. 2007).

3. Confocal Microscopy Analysis

Fifty mM sodium azide was added to synchronized L3 stage worms, and the worms were cultured for 5 minutes. Worms treated under each condition were placed on 3% agar on a glass slide for microscopic observation. For fluorescence observation, an LSM700 confocal microscope (ZEISS, Jena, Germany) equipped with a FITC filter was used. All images were 8-bit and analyzed using ZEN Black software (ZEISS).

4. RNA Extraction and cDNA Synthesis

Synchronized L3 stage worms were incubated on NGM plates and washed 3 times with S-basal and 1 time with water for collection. TRIzol was added to a pellet and frozen in nitrogen gas. Proteins and other impurities were removed by addition of chloroform, and RNA was precipitated with isopropyl alcohol. RNA concentration was measured with an ND-1000 spectrophotometer. cDNA was synthesized using a GE Healthcare kit. cDNA was additionally purified, and the RNA concentration was measured using the ND-1000 spectrophotometer.

5. Quantitative RT-PCR (qRT-PCR)

Total RNA was isolated from the sample as described in the manual using

RNAspin mini columns (GE Healthcare, UK), and 2 μg of manually provided RNA was transcribed using a transcriptor first standard cDNA synthesis kit (Roche, IN, USA) along with oligoDT priming. qRT-PCR was performed using SYBR Green PCR Master Mix (Qiagen) according to the manufacturer's manual.

<EXAMPLE 2> CHARACTERIZATION OF RCAT IN HUMAN CELL LINE

1. Cell Line

Figure 4:
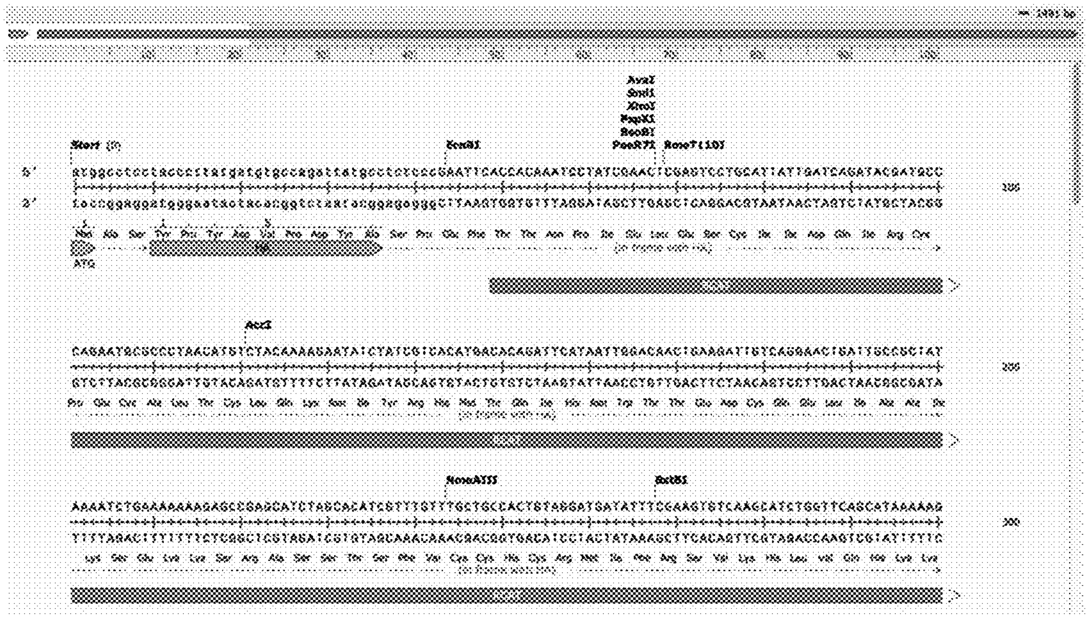
FIG. 4 illustrates an HA-RCAT portion, which is a junction part between a plasmid vector and RCAT gene in pcDNA3.1-HA-RCAT that is transfected into a human HEK293T cell line. The corresponding drawing was produced using a Snapgene (GSL Biotech, CA, USA) program.

HEK293T cells (Korean Cell Line Bank, 21573) were maintained under conditions of 37° C. and 5% $CO_2$ in a Dulbecco's Modified Eagle Medium (DMEM; Hyclone, HS3243.01) supplemented with 10% fetal bovine serum (Hyclone, SV30087.02) and 1% penicillin-streptomycin (Biowest, L0022). The expression vectors transfected into the cell line are as follows: Flag-Keap1 (Addgene, MA, USA); pCDNA3-Myc3-Nrf2 (Addgene, MA, USA); and pcDNA3.1-HA-RCAT. The expression vector pCDNA3.1-HA-RCAT was constructed by conjugating *Caenorhabditis elegans* RCAT cDNA with pcDNA3.1-HA (Addgene, MA, USA). The conjugated site of the corresponding expression vector is shown in FIG. 4. The RCAT cDNA sequence inserted into the expression vector is set forth in SEQ ID NO: 3.

2. Immunoblot Analysis

For immunoprecipitation (IP), HEK293T cells were lysed in a lysis buffer (including 50 mM Tris-HCl (pH 7.5), 125 mM NaCl, 1 mM phenylmethylsulfonyl fluoride (PMSF), 10% glycerol, 0.3% TritonX-100, 1 mM ethylenediaminetetraacetic acid (EDTA), 0.5% Nonidet P-40 (NP-40), 10 mM β-phosphoglyceride, 1 mM $Na_3V0_4$, 5 mM NaF and 1 mg/mL aprotinin and leupeptin). A cell lysate was centrifuged and IP was applied to the resulting supernatant with an antibody against FLAG HA or Myc using protein G-sepharose beads.

For immunoblotting, sodium dodecyl sulfate polyacrylamide gel electrophoresis was performed on the cell lysates or immunoprecipitates, and an isolated protein was transferred to a polyvinylidene difluoride membrane, incubated with a primary antibody at 4° C. overnight, and then incubated with a horseradish peroxidase-conjugated secondary antibody at room temperature for 1 hour. Visualization was performed using an enhanced chemiluminescence lightning solution (Thermo Fisher Scientific).

3. Luciferase Reporter Analysis

Nrf2 activity was measured by dual luciferase after transfection of a reporter plasmid including an antioxidant response element (ARE) and a canonical Nrf2 binding motif HEK293T cells were transfected with an expression vector for RCAT, Keap1 and Nrf2 along with a pNqo1-ARE reporter plasmid (provided by H.-S. Choi) and pRL-TK (endogenous control, Promega) for 24 hours. And then, luciferase activity was analyzed from the cells using a dual luciferase reporter gene analysis system (Promega).

<EXPERIMENTAL EXAMPLE 1> IDENTIFICATION OF CORRELATION OF RCAT (ok1745) STRAIN WITH ROS

Figure 1:
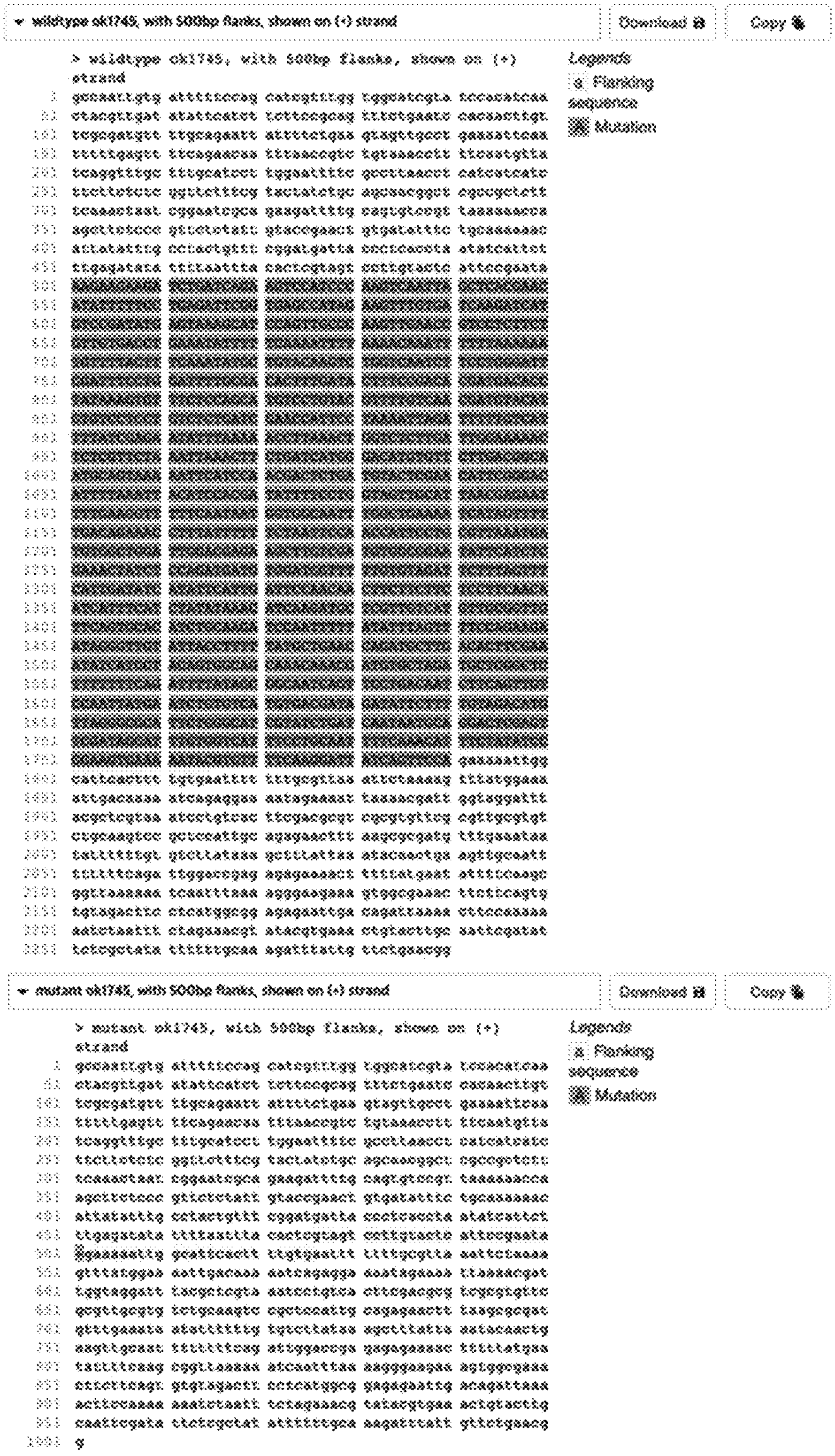
FIG. 1 illustrates the results of from comparison of a gene deletion site in an RCAT mutant (ok1745) with a wild type (left side of FIG. 1: SEQ ID NO: 2) and an RCAT mutant (right side of FIG. 1: SEQ ID NO: 1). The corresponding drawing was adopted from the data of wormbase.org.

FIG. 1 illustrates the results of comparing a gene deletion site of an RCAT mutant (ok1745) with a wild type (left side of FIG. 1: SEQ ID NO: 2) and an RCAT mutant (right side of FIG. 1: SEQ ID NO: 1). The corresponding drawing was adopted from the data of wormbase.org.

Further, as a result of measuring ROS generation amounts using DCFDA assay in a normal wild type and an RCAT mutant in order to identify the antioxidant effect of RCAT, as illustrated in FIG. 2, it was confirmed that more ROS were generated in the RCAT mutant.

In addition, the expression level of oxidative stress-related genes known to be regulated by SKN-1 was measured using QRT-PCR in order to identify whether such ROS generation is associated with the oxidative stress-related transcriptional factor Nrf2/SKN-1.

As illustrated in FIG. 3, it was found that the expression of oxidative stress-related genes known to be regulated by SKN-1 was reduced in the RCAT mutant and recovered in the overexpressed species.

Furthermore, it is known that human Nrf2 binds to Keap1 to be degraded in a normal situation, and when oxidative stress is applied, free Nrf2 enters the nucleus while the bond between the two is broken, thereby regulating the transcription of oxidative stress-related genes. In order to identify whether the action of RCAT and Nrf2/SKN-1 occurs not only in *Caenorhabditis elegans*, but also in a human cell line, the interaction was observed by expressing RCAT and Nrf2 in the HEK239T cell line.

As illustrated in FIG. 5, it was found that when RCAT was added, Keap1 bound to RCAT instead of Nrf2, and accordingly, a lot of Nrf2 freely entering the nucleus was demonstrated.

It was confirmed through western blot whether free Nrf2 is actually generated by the action of RCAT in a human HEK293T cell line and enters the nucleus.

As illustrated in FIG. 6, it can be seen that the detection amount of Keap1 decreases as the amount of injected RCAT increases, meaning that a Keap1-RCAT complex is degraded by binding to the injected RCAT. Further, through the fact that the larger the injection amount of RCAT, more Nrf2 in the nucleus is detected, it is confirmed that RCAT binds to Keap1 instead of Nrf2, and accordingly, Nrf2 freely enters the nucleus.

In addition, in order to identify whether the transactivation activity of Nrf2 is actually generated by RCAT in the human HEK293T cell line, M-Nrf2, F-Keap1 and H-RCAT were expressed in the HEK293T cell line with the luciferase reporter plasmid pNqo-1 ARE.

As illustrated in FIG. 7, the transactivation activity of Nqo-1 is increased by Nrf2, and is decreased by Keap1 known as a suppressor of Nrf2.

Furthermore, it was observed that RCAT bound to Keap1 to degrade Keap1, thereby increasing the transactivation activity of Nqo-1 by Nrf2.

What is claimed is:

1. A model for oxidative stress research, selected from a group consisting of *Caenorhabditis elegans* R02D3.7 (ok1745) comprising a regulator of cat (RCAT) gene deletion mutant having a base sequence of SEQ ID NO: 1; and a human HEK293T cell line expressing RCAT and Nrf2, wherein the human HEK293T cell line expressing RCAT and Nrf2 is transfected with a wild-type RCAT gene derived from *Caenorhabditis elegans* and a human Nrf2 gene.

2. The model of claim 1, wherein the RCAT gene deletion mutant has a mutation in which a site having a base sequence of SEQ ID NO: 4 is deleted in a wild-type RCAT gene having a base sequence of SEQ ID NO: 2.

3. The model of claim 1, wherein the *Caenorhabditis elegans* R02D3.7 (ok1745) has an increased generation amount of reactive oxygen species (ROS) compared to a wild-type *Caenorhabditis elegans* comprising a wild-type RCAT gene having a base sequence of SEQ ID NO: 2.

4. The model of claim 1, wherein the wild-type RCAT gene has a base sequence of SEQ ID NO: 2 or 3.

5. An antioxidant composition comprising a regulator of cat (RCAT) gene having a base sequence of SEQ ID NO: 2 or 3.

6. A method for screening an antioxidant drug, the method comprising:

treating of the model for oxidative stress research of claim 1, with an antioxidant candidate drug; and measuring whether a generation amount of reactive oxygen species (ROS) is reduced in the model, wherein the model is *Caenorhabditis elegans* R02D3.7 (ok1745) comprising a regulator of cat (RCAT) gene deletion mutant having a base sequence of SEQ ID NO: 1.

* * * * *